United States Patent
Heidenfelder et al.

(10) Patent No.: US 6,887,460 B2
(45) Date of Patent: May 3, 2005

(54) COSMETIC OR PHARMACEUTICAL PREPARATIONS WHICH COMPRISE ENAMINOTRIAZINES AS LIGHT PROTECTION AGENTS, AND NOVEL ENAMINOTRIAZINES

(75) Inventors: Thomas Heidenfelder, Dannstadt (DE); Kristin Tiefensee, Bad Duerkheim (DE); Thomas Wünsch, Speyer (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/142,974

(22) Filed: May 13, 2002

(65) Prior Publication Data

US 2003/0044363 A1 Mar. 6, 2003

(30) Foreign Application Priority Data

May 18, 2001 (DE) .......................................... 101 24 332

(51) Int. Cl.$^7$ ................................................. A61K 7/42
(52) U.S. Cl. ........................... 424/59; 424/60; 424/64; 424/70.1
(58) Field of Search ............................. 424/59, 60, 64, 424/70.1, 401

(56) References Cited

U.S. PATENT DOCUMENTS

| | | | |
|---|---|---|---|
| 5,236,698 A | 8/1993 | Richard et al. | 424/47 |
| 5,849,909 A | 12/1998 | Richard et al. | 544/197 |
| 5,928,630 A | 7/1999 | Richard et al. | 424/59 |
| 5,945,091 A | 8/1999 | Habeck et al. | 424/59 |
| 6,037,487 A | 3/2000 | Habeck et al. | 558/449 |

FOREIGN PATENT DOCUMENTS

| | | |
|---|---|---|
| EP | 507691 | 10/1992 |
| EP | 790243 | 8/1997 |
| EP | 0 852 137 | 7/1998 |
| EP | 0 895 776 | 2/1999 |
| WO | WO 98/47893 | 10/1998 |
| WO | WO 99/02495 | 1/1999 |

OTHER PUBLICATIONS

Kreutzberger et al. "Triazines. XXIII. The Reaction of s–Triazine with Active Methylene Compounds" Cosmetic Colorants from Dyes Commission of German Research Society vol. 26 (1984) pp. 1121–1126.

Hashida et al. "Preparation and Reaction of Isocyano–1,3, 5–triazines" J. Heterocyclic Chem. vol. 26 (1989) pp. 901–905.

Primary Examiner—Jyothsna Venkat
(74) Attorney, Agent, or Firm—Keil & Weinkauf

(57) ABSTRACT

The invention relates to the use of enaminotriazines of the formula I

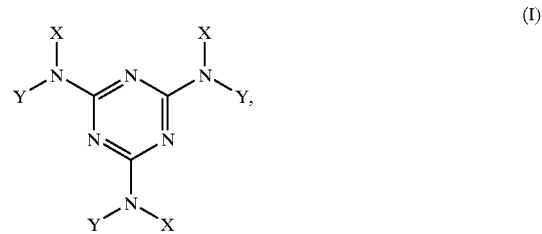

in which the radicals Y, independently of one another, are hydrogen, an optionally substituted aliphatic, cycloaliphatic, araliphatic or aromatic radical having in each case up to 18 carbon atoms, the radicals X are identical or different, where at least one of the radicals X is the ethenyl radical of the formula II

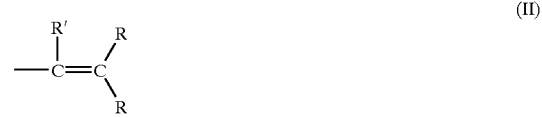

and X may also have the meanings of Y, and where in the formula II the radicals R are identical or different and are cyano, optionally esterified carboxyl, substituted carbonyl, optionally substituted aminocarbonyl, optionally esterified sulfo, substituted sulfonyl or optionally esterified phosphono, and where two adjacent radicals R may optionally form a ring and the radicals R' are identical or different and are hydrogen, an optionally substituted aliphatic, cycloaliphatic or aromatic radical having in each case up to 18 carbon atoms, as UV filters in cosmetic or pharmaceutical preparations for protecting human skin or human hair against solar rays, alone or together with compounds which absorb in the UV region and which are known per se for cosmetic preparations.

8 Claims, No Drawings

COSMETIC OR PHARMACEUTICAL PREPARATIONS WHICH COMPRISE ENAMINOTRIAZINES AS LIGHT PROTECTION AGENTS, AND NOVEL ENAMINOTRIAZINES

Cosmetic or pharmaceutical preparations which comprise enaminotriazines as light protection agents, and novel enaminotriazines The invention relates to the use of substituted enaminotriazines as UV filters alone or together with further UV filters in cosmetic and pharmaceutical preparations, and to novel enaminotriazines.

The light protection agents used in cosmetic and pharmaceutical preparations have the task of preventing, or at least reducing the consequences of, harmful effects of sunlight on the human skin. In addition, these light protection agents also, however, serve to protect further ingredients against decomposition or degradation by UV radiation. In hair cosmetic formulations, the aim is to reduce damage to the keratin fibers by UV rays.

The sunlight which reaches the surface of the earth has a content of UV-B radiation (280 to 320 nm) and of UV-A radiation (>320 nm), which directly border the visible light region. The effect on the human skin becomes evident, particularly in the case of UV-B radiation, from sunburn. Accordingly, the industry offers a relatively large number of substances which absorb UV-B radiation and thus prevent sunburn.

Dermatological investigations have now shown that UV-A radiation is also perfectly capable of causing skin damage and allergies, by, for example, damaging the keratin or elastin. This reduces the elasticity and water-storability of the skin, i.e. the skin becomes less supple and tends to form wrinkles. The noticeably high incidence of skin cancer in areas of strong solar irradiation shows that damage to the genetic information in the cells is evidently also caused by sunlight, specifically by UV-A radiation. All of these findings therefore suggest the need to develop efficient filter substances for the UV-A and UV-B regions.

There is a growing need for light protection agents for cosmetic and pharmaceutical preparations whose absorption maxima should be in the range from about 280 to 380 nm. In order to achieve the desired effect using the lowest possible amount, light protection agents of this type should additionally have a high specific absorbance. Furthermore, light protection agents for cosmetic preparations must also satisfy a large number of further requirements, for example good ability to be formulated in cosmetic preparations, high stability of the emulsions prepared therewith, toxicological acceptability, and low intrinsic odor and low intrinsic color.

Although a large number of UV light protection agents are already known, the combination of the properties of high absorbance in the UV-A and/or UV-B region and photostability has been realized only to an unsatisfactory degree. There is therefore a need for UV filters which realize these requirements to a particularly high degree.

It is an object of the invention to provide novel light protection agents which satisfy these requirements. We have found that this object is achieved by the use of enaminotriazines of the formula I

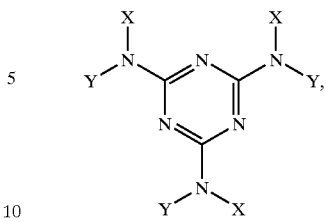

in which the radicals Y, independently of one another, are hydrogen, an optionally substituted aliphatic, cycloaliphatic, araliphatic or aromatic radical having in each case up to 18 carbon atoms, the radicals X are identical or different, where at least one of the radicals X is the ethenyl radical of the formula II

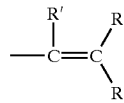

and X may also be hydrogen, and where in the formula II, the radicals R are identical or different and are cyano, optionally esterified carboxyl, substituted carbonyl, optionally substituted aminocarbonyl, optionally esterified sulfo, substituted sulfonyl or optionally esterified phosphono (i.e. the radical (HO)$_2$OP—), and where two adjacent radicals R can optionally form a ring, and the radicals R' are identical or different and are hydrogen, an optionally substituted aliphatic, cycloaliphatic or aromatic radical having in each case up to 18 carbon atoms, as UV filters in cosmetic or pharmaceutical preparations for protecting human skin or human hair against solar rays, alone or together with compounds which absorb in the UV region and which are known per se for cosmetic preparations.

In this connection, preference is given to the use of compounds of the formula I in which Y is hydrogen and one or more of the radicals X are an ethenyl radical of the formula IIa

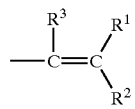

in which the radicals $R^1$ and $R^2$ are identical or different and are —COOR$^4$, —COR$^4$, —CON(R$^4$)$_2$, —CN, —SO$_2$R$^4$, —SO$_2$OR$^4$ or —PO(OR$^4$)$_2$, where the radicals R$^4$, independently of one another, are hydrogen, an aliphatic, cycloaliphatic, araliphatic or aromatic radical, each of which may be optionally substituted, and where adjacent radicals $R^1$ and $R^2$ may optionally form a ring and $R^3$ is hydrogen or an aliphatic, cycloaliphatic, araliphatic or aromatic radical, each of which may be substituted.

Particular preference is given to compounds of the formula I in which $R^3$ is hydrogen, $R^1$ and $R^2$ are identical or different and —COOR$^5$, —COR$^5$ or —CN, where R$^5$ is an aliphatic or optionally substituted aromatic radical having up to 18 carbon atoms.

The invention equally relates to cosmetic or pharmaceutical preparations comprising light protection agents for protecting human skin or human hair against solar rays, alone or together with compounds which absorb in the UV region and which are known per se for cosmetic preparations and which comprise, as essential UV filters, effective amounts of enaminotriazines of the formula I

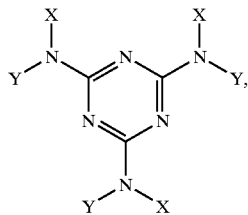

in which the radicals Y, independently of one another, are hydrogen, an optionally substituted aliphatic, cycloaliphatic, araliphatic or aromatic radical having in each case up to 18 carbon atoms, the radicals X are identical or different, where at least one of the radicals X is the ethenyl radical of the formula II

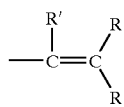

and X may also be hydrogen, and where in the formula II the radicals R are identical or different and are cyano, optionally esterified carboxyl, substituted carbonyl, optionally substituted aminocarbonyl, optionally esterified sulfo, substituted sulfonyl or optionally esterified phosphono, and where two adjacent radicals R may optionally form a ring, and the radicals R' are identical or different and are hydrogen, an optionally substituted aliphatic, cycloaliphatic or aromatic radical having in each case up to 18 carbon atoms.

Finally, the invention also relates to tris(ethenylamino) triazines of the formula III as novel compounds

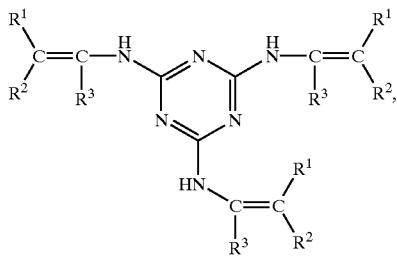

in which the radicals $R^1$ and $R^2$ are identical or different and are —COOR$^4$, —COR$^4$, —CON(R$^4$)$_2$, —CN, —SO$_2$R$^4$, —SO$_2$OR$^4$ or —PO(OR$^4$)$_2$, where the radicals $R^4$, independently of one another, are hydrogen, an aliphatic, cycloaliphatic, araliphatic or aromatic radical, each of which may be optionally substituted, and where two adjacent radicals R may optionally form a ring and $R^3$ is hydrogen or an aliphatic, cycloaliphatic, araliphatic or aromatic radical, each of which may be substituted.

In all of the abovementioned compounds, the enamine group may be in the E or Z configuration.

Enaminotriazines are known from a number of literature sources, e.g. from Hashida, Y; Imai, A.; Sekiguchi, S; J. Heterocyclic Chem. 1989, 26, 901–5, WO 99/02495 and WO 9847893.

In addition, Kreutzberger, A; Grundmann, C; J. Org. Chem. 1961, 4, 1121–1126 has already described enamino (hexahydro)triazines. In none of these literature sources is the use of these compounds as light protection agents in cosmetic preparations disclosed or suggested.

Finally, aromatics carrying enamino substituents are known as light protection agents in cosmetic preparations from EP-A 895 776 and EP-A 852 137. The latter specification also gives the general information that the aromatic radical may also be a heteroaromatic.

However, it could not be deduced from these literature sources that the enaminotriazines to be used according to the invention are characterized by their particularly advantageous properties, such as very high absorbance and high photostability.

Particular preference is given to the use of compounds of the formula I in which $R^3$ is hydrogen and $R^1$ and $R^2$, independently of one another, are CN, COOR$^4$ and COR$^4$, where $R^4$ is identical or different open-chain or branched aliphatic or optionally substituted, aromatic radicals having up to 8 carbon atoms.

Suitable substituents are lipophilic and also hydrophilic substituents having e.g. up to 20 carbon atoms. Lipophilic radicals, i.e. radicals which boost the solubility in oil of the compounds of the formula I, are, for example aliphatic or cycloaliphatic radicals, in particular alkyl radicals having 1 to 18 carbon atoms, alkoxy, mono- and dialkylamino, alkoxycarbonyl, mono- and dialkylaminocarbonyl, mono- and dialkylaminosulfonyl radicals, and also cyano, nitro, bromo, chloro, iodo or fluoro substituents.

Hydrophilic radicals, i.e. radicals which allow the compounds of the formula I to dissolve in water, are, for example, carboxyl and sulfoxy radicals and, in particular, salts thereof with any physiologically compatible cations, such as the alkaline metal salts or the trialkylammonium salts, such as tri(hydroxyalkyl)ammonium salts or the 2-methylpropan-1-ol-2-ammonium salts. Also suitable are alkylammonium radicals having any physiologically compatible anions. Low-solubility compounds of the formula I can be used in micronized form in cosmetic preparations.

Suitable alkoxy radicals are those having 1 to 12 carbon atoms, preferably having 1 to 8 carbon atoms.

Examples which may be mentioned are:

| | |
|---|---|
| methoxy | isopropoxy |
| n-propoxy | 1-methylpropoxy |
| n-butoxy | n-pentoxy |
| 2-methylpropoxy | 3-methylbutoxy |
| 1,1-dimethylpropoxy | 2,2-dimethylpropoxy |
| hexoxy | 1-methyl-1-ethylpropoxy |
| heptoxy | octoxy |
| 2-ethylhexoxy | |

Suitable mono- or dialkylamino radicals are, for example, those which contain alkyl radicals having 1 to 8 carbon atoms, such as methyl, n-propyl, n-butyl, 2-methylpropyl, 1,1-dimethylpropyl, hexyl, heptyl, 2-ethylhexyl, isopropyl, 1-methylpropyl, n-pentyl, 3-methylbutyl, 2,2-dimethylpropyl, 1-methyl-1-ethylpropyl and octyl. These radicals are equally present in the mono- and dialkylaminocarbonyl and sulfonyl radicals.

The compounds of the formulae I and III to be used according to the invention can be prepared in accordance with the equation by reacting a compound having an activated methylene group with melamine in the presence of orthoformate according to the following scheme

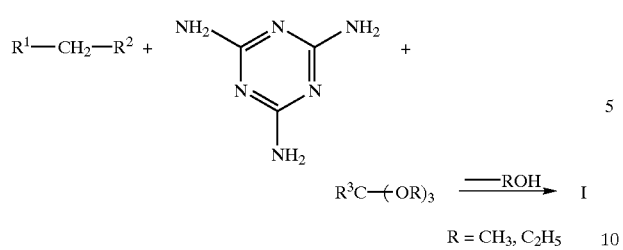

$$R = CH_3, C_2H_5$$

by condensation in a manner known per se, where $R^1$ to $R^3$ have the above meanings.

Examples of compounds $R^1$—$CH_2$—$R^2$ containing active methylene groups are cyanoacetic esters, cyanoacetamides, cyanoacetic acid, malonic esters, malonamides, malonic acid, acetoacetic esters, acetoacetamides, acetoacetic acid, 1,3-diketones, malodinitrile and α-cyanoketones.

Depending on how the ratio of the methylene compound (and orthoformate) to melamine is chosen, mono-, di- or trisubstitution of the melamine is achieved. Preference is given to the reaction with an at least 3-fold molar amount, so that the trisubstituted compound is predominantly obtained. Details of the synthesis method are given in the information in EP-A 0 852 137.

The cosmetic and pharmaceutical preparations which comprise light protection agents are usually based on a carrier which comprises at least one oil phase. However, preparations merely based on water are also possible if compounds with hydrophilic substituents are used. Accordingly, suitable preparations are oils, oil-in-water and water-in-oil emulsions, creams and pastes, lipcare stick compositions or grease-free gels.

Sunscreen preparations of this type can, accordingly, be in liquid, paste or solid form, for example as water-in-oil creams, oil-in-water creams and lotions, aerosol foam creams, gels, oils, wax pencils, powders, sprays or alcoholic-aqueous lotions.

Examples of customary oil components in cosmetics are paraffin oil, glyceryl stearate, isopropyl myristate, diisopropyl adipate, cetylstearyl 2-ethylhexanoate, hydrogenated polyisobutene, Vaseline, caprylic/capric triglycerides, microcrystalline wax, lanolin and stearic acid.

Customary cosmetic auxiliaries which may be suitable as additives are, for example, coemulsifiers, fats and waxes, stabilizers, thickeners, biogenic active ingredients, film formers, fragrances, dyes, pearlizing agents, preservatives, pigments, electrolytes (e.g. magnesium sulfate) and pH regulators. Suitable coemulsifiers are preferably known W/O and also O/W emulsifiers such as, for example, polyglycerol esters, sorbitan esters or partially esterified glycerides. Typical examples of fats are glycerides; waxes which may be mentioned are, inter alia, beeswax, paraffin wax or microcrystalline waxes, possibly in combination with hydrophilic waxes. Stabilizers which can be used are metal salts of fatty acids such as, for example, magnesium, aluminum and/or zinc stearate. Suitable thickeners are, for example, crosslinked polyacrylic acids and derivatives thereof, polysaccharides, in particular xanthan gum, guar guar, agar agar, alginates and tyloses, carboxymethylcellulose and hydroxyethylcellulose and also fatty alcohols, monoglycerides and fatty acids, polyacrylates, polyvinyl alcohol and polyvinylpyrrolidone. Examples of biogenic active ingredients are plant extracts, protein hydrolysates and vitamin complexes. Examples of customary film formers are hydrocolloids such as chitosan, microcrystalline chitosan or quaternized chitosan, polyvinylpyrrolidone, vinylpyrrolidone-vinyl acetate copolymers, polymers of the acrylic acid series, quaternary cellulose derivatives and similar compounds. Examples of suitable preservatives are formaldehyde solution, p-hydroxybenzoate or sorbic acid. Examples of pearlizing agents are glycol distearic esters such as ethylene glycol distearate, but also fatty acids and fatty acid monoglycol esters. Dyes which can be used are the substances suitable and approved for cosmetic purposes, as listed, for example, in the publication "Kosmetische Färbemittel" [Cosmetic Colorants] from the Farbstoffkommission der Deutschen Forschungsgemeinschaft, [Dyes Commission of the German Research Society], published in Verlag Chemie, Weinheim, 1984. These dyes are normally used in concentrations of from 0.001 to 0.1% by weight, based on the total mixture.

The total content of auxiliaries and additives can be from 1 to 80% by weight, preferably from 6 to 40% by weight, and the nonaqueous fraction ("active substance") can be from 20 to 80% by weight, preferably from 30 to 70% by weight, based on the compositions. The compositions can be prepared in a manner known per se, i.e. for example by hot, cold, hot-hot/cold or PIT emulsification. This is a purely mechanical process; no chemical reaction takes place.

Finally, it is also possible to co-use other substances which absorb in the UV-A region and are known per se, provided they are stable in the overall system of the combination of UV-B and UV-A filters to be used according to the invention.

The present invention further provides cosmetic and pharmaceutical preparations which comprise 0.1 to 10% by weight, preferably 1 to 7% by weight, based on the total amount of the cosmetic and pharmaceutical preparation, of one or more compounds of the formula I together with compounds which absorb in the UV-B region and which are known per se for cosmetic and pharmaceutical preparations, as light protection agents, where the compounds of the formula I are generally used in a lesser amount than the UB-B-absorbing compounds.

Suitable UV-B filter substances which are used in combination with the compounds of the formula I to be used according to the invention are any UV-B filter substances. Examples which may be mentioned are:

| No. | Substance | CAS No. (= acid) |
|---|---|---|
| 1 | 4-Aminobenzoic acid | 150-13-0 |
| 2 | 3-(4'-Trimethylammonium)benzylidenebornan-2-one methylsulfate | 52793-97-2 |
| 3 | 3,3,5-Trimethylcyclohexyl salicylate (homosalate) | 118-56-9 |
| 4 | 2-Hydroxy-4-methoxybenezophenone (oxybenzone) | 131-57-7 |
| 5 | 2-Phenylbenzimidazole-5-sulfonic acid and its potassium, sodium and triethanolamine salts | 27503-81-7 |
| 6 | 3,3'-(1,4-Phenylenedimethine)bis(7,7-dimethyl-2-oxobicyclo[2.2.1]heptane-1-methanesulfonic acid) and its salts | 90457-82-2 |
| 7 | Polyethoxyethyl 4-bis(polyethoxy)aminobenzoate | 113010-52-9 |
| 8 | 2-Ethylhexyl 4-dimethylaminobenzoate | 21245-02-3 |
| 9 | 2-ethylhexyl salicylate | 118-60-5 |
| 10 | Isoamyl 4-methoxycinnamate | 7/6/7-10-2 |
| 11 | 2-Ethylhexyl 4-methoxycinnamate | 5466-77-3 |
| 12 | 2-Hydroxy-4-methoxybenzophenone-5-sulfonic acid (sulisobenzone) and the sodium salt | 4065-45-6 |
| 13 | 3-(4'-Sulfobenzylidene)bornan-2-one and salts | 58030-58-6 |
| 14 | 3-(4'-Methylbenzylidene)bornan-2-one | 36861-47-9 |
| 15 | 3-Benzylidenebornan-2-one | 16087-24-8 |

-continued

| No. | Substance | CAS No. (= acid) |
|---|---|---|
| 16 | 1-(4'-Isopropylphenyl)-3-phenylpropane-1,3-dione | 63260-25-9 |
| 17 | 4-Isopropylbenzyl salicylate | 94134-93-7 |
| 18 | 2,4,6-Trianilino(o-carbo-2'-ethylhexyl-1'-oxy)-1,3,5-triazine | 88122-99-0 |
| 19 | 3-Imidazol-4-yl-acrylic acid and its ethyl ester | 104-98-3* |
| 20 | Ethyl 2-cyano-3,3-diphenylacrylate | 5232-99-5 |
| 21 | 2'-Ethylhexyl 2-cyano-3,3-diphenylacrylate | 6197-30-4 |
| 22 | Methyl o-aminobenzoate or: 5-methyl-2-(1-methylethyl)-2-aminobenzoate | 134-09-8 |
| 23 | Glyceryl p-aminobenzoate or: 1-glyceryl 4-aminobenzoate | 136-44-7 |
| 24 | 2,2'-Dihydroxy-4-methoxybenzophenone-(dioxybenzone) | 131-53-3 |
| 25 | 2-Hydroxy-4-methoxy-4-methylbenzophenone-(Mexenone) | 1641-17-4 |
| 26 | Triethanolamine salicylate | 2174-16-5 |
| 27 | Dimethoxyphenylglyoxalic acid or: sodium 3,4-dimethoxyphenylglyoxalate | |
| 28 | 3-(4'-Sulfobenzylidene)bornan-2-one and its salts | 56039-58-8 |

If, on the other hand, the compound of the formula I to be used according to the invention is a UV-B filter, it can of course also be combined with UV-A filters or else broadband absorbers known per se.

Examples of such UV-A and broadband absorbers are

| No. | Substance | CAS No. (= acid) |
|---|---|---|
| 29 | 1,1-Bis(neopentyloxycarbonyl)-4,4-diphenyl-1,3-butadiene | according to EPA 916335 |
| 30 | n-Hexyl 2-(4'-diethylamino-2'-hydroxybenzoyl)-benzoate | 302776-68-7 |
| 31 | 2,2'-Methylenebis[6-(2H-benzotriazol-2-yl)-4-(1,1,3,3-tetramethylbutyl)phenol (Tinosorb ® M) | 103597-45-1 |
| 32 | 2,2'-[6-Methoxyphenyl)-1,3,5-triazin-2,4-diyl]-bis[5-[(2-ethylhexyl)oxy]phenol (Tinosorb ® S) | 187393-00-6 |
| 33 | 2-[5,6-Disulfo(1H-benzimidazol-2-yl)phenyl]-1H-benzimidazole-5,6-disulfonic acid | 180898-37-7 |
| 34 | 2-(2H-1,2,3-Benzotriazol-2-yl)-4-methyl-6-(2-methyl-3-[1,3,3,3-tetramethyl-1-[trimethylsilyl)oxy]disiloxanyl]propyl)phenol | 155633-54-8 |

Finally, mention may also be made of micronized pigments such as titanium dioxide and zinc oxide.

To protect human hair from UV rays, the light protection agents of the formula I according to the invention can be incorporated into shampoos, lotions, gels or emulsions in concentrations of from 0.1 to 10% by weight, preferably from 1 to 7% by weight. The respective formulations can be used, inter alia, for washing, coloring and for styling the hair.

The compounds to be used according to the invention are usually characterized by a particularly high absorbance. Furthermore, they are readily soluble in cosmetic oils and can be readily incorporated into cosmetic formulations. The emulsions prepared with the compounds I are characterized in particular by their high stability, the compounds I themselves by their high photostability, and the preparations prepared with I by their pleasant feel on the skin.

The pharmaceutical use according to the invention essentially relates to topical application. Application is, for example, in the form of an ointment, cream, gel, spray, solution or lotion.

EXAMPLES

I. Preparation

Example 1

0.1 mol of melamine, 0.3 mol of ethyl cyanoacetate and 0.3 mol of triethyl orthoformate were heated at 120° C. for 11 h, and ethanol distilled off. After cooling, 200 ml of ethanol were added, and the precipitate formed was filtered off. The residue was washed with petroleum ether and dried at 50° C. under reduced pressure. This gave 29.1 g (59%) of the compound of the formula III in which $R^3$ is hydrogen, $R^1$ is cyano and $R^2$ is ethyloxycarbonyl ($\lambda_{max}$=318 nm; $E_1^1$=1784)

In an analogous way, highly active compounds of the formula I are obtained if the activated methylene compounds used as starting compounds are the following compounds:
methyl acetoacetate
ethyl acetoacetate
2-ethylhexyl acetoacetate
acetylacetone
dibenzoylmethane
pivaloylacetonitrile
dimethyl malonate
diethyl malonate
di(2-ethylhexyl) malonate
benzoylacetonitrile
benzoxazol-2-ylacetonitrile
benzoxazol-2-ylacetic acid
methyl benzoxazol-2-ylacetate
ethyl benzoxazol-2-ylacetate
2-ethylhexyl benzoxazol-2-ylacetate
methylcyanoacetate
2-ethylhexyl cyanoacetate
1-phenyl-1,3-butanedione
benzoylacetonitrile
malodinitrile
indane-1,3-dione
2,2-dimethyl-1,3-dioxane-4,6-dione (Meldrum's acid)
sulfonyldiacetonitrile
2-benzimidazoylacetonitrile
(1H-benzimidazol-2-yl)acetic acid
methyl (1H-benzimidazol-2-yl)acetate
ethyl (1H-benzimidazol-2-yl)acetate
2-ethylhexyl (1H-benzimidazol-2-yl)acetate General preparation procedure for the preparation of emulsions for cosmetic purposes All of the oil-soluble constituents are heated to 85° C. in a stirred vessel. When all of the constituents are molten, or are in the form of a liquid phase, the water phase is incorporated with homogenization. While being stirred, the emulsion is cooled to about 40° C., perfumed, homogenized and then cooled to 25° C. with continuous stirring.

Preparations

Example 2

Composition for Lip Care

| | |
|---|---|
| ad 100 | Eucerinum anhydricum |
| 10.00 | Glycerol |
| 10.00 | Titanium dioxide |
| 1.00 | Compound of Example 1 |
| 8.00 | Octyl methoxycinnamate |

-continued

| | |
|---|---|
| 5.00 | Zinc oxide |
| 4.00 | Castor oil |
| 4.00 | Pentaerythrityl stearate/caprate/caprylate/adipate |
| 3.00 | Glyceryl stearate SE |
| 2.00 | Beeswax |
| 2.00 | Microcrystalline wax |
| 2.00 | Quaternium-18 bentonite |
| 1.50 | PEG-45/dodecyl glycol copolymer |

Example 3

Composition for Lip Care

| | |
|---|---|
| ad 100 | Eucerinum anhydricum |
| 10.00 | Glycerol |
| 10.00 | Titanium dioxide |
| 1.50 | Compound of Example 1 |
| 8.00 | Octyl methoxycinnamate |
| 5.00 | Zinc oxide |
| 4.00 | Castor oil |
| 4.00 | Pentaerythrityl stearate/caprate/caprylate/adipate |
| 3.00 | Glyceryl stearate SE |
| 2.00 | Beeswax |
| 2.00 | Microcrystalline wax |
| 2.00 | Quaternium-18 bentonite |
| 1.50 | PEG-45/dodecyl glycol copolymer |

Example 4

Composition for Sunblock Containing Micropigments

| | |
|---|---|
| ad 100 | Water |
| 10.00 | Octyl methoxycinnamate |
| 6.00 | PEG-7 hydrogenated castor oil |
| 6.00 | Titanium dioxide |
| 3.00 | Compound of Example 1 |
| 5.00 | Mineral oil |
| 5.00 | Isoamyl p-methoxycinnamate |
| 5.00 | Propylene glycol |
| 3.00 | Jojoba oil |
| 3.00 | 4-Methylbenzylidenecamphor |
| 2.00 | PEG-45/dodecyl glycol copolymer |
| 1.00 | Dimethicone |
| 0.50 | PEG-40 hydrogenated castor oil |
| 0.50 | Tocopheryl acetate |
| 0.50 | Phenoxyethanol |
| 0.20 | EDTA |

Example 5

Composition for Sunblock Containing Micropigments

| | |
|---|---|
| ad 100 | Water |
| 10.00 | Octyl methoxycinnamate |
| 6.00 | PEG-7 hydrogenated castor oil |
| 6.00 | Titanium dioxide |
| 2.00 | Compound of Example 1 |
| 5.00 | Mineral oil |
| 5.00 | Isoamyl p-methoxycinnamate |
| 5.00 | Propylene glycol |
| 3.00 | Jojoba oil |
| 3.00 | 4-Methylbenzylidenecamphor |
| 2.00 | PEG-45/dodecyl glycol copolymer |
| 1.00 | Dimethicone |
| 0.50 | PEG-40 hydrogenated castor oil |

-continued

| | |
|---|---|
| 0.50 | Tocopheryl acetate |
| 0.50 | Phenoxyethanol |
| 0.20 | EDTA |

Example 6

Grease-free Gel

| | |
|---|---|
| ad 100 | Water |
| 8.00 | Octyl methoxycinnamate |
| 7.00 | Titanium dioxide |
| 1.50 | Compound of Example 1 |
| 5.00 | Glycerol |
| 5.00 | PEG-25 PABA |
| 1.00 | 4-Methylbenzylidenecamphor |
| 0.40 | Acrylate $C_{10}$–$C_{30}$ alkyl acrylate crosspolymer |
| 0.30 | Imidazolidinylurea |
| 0.25 | Hydroxyethylcellulose |
| 0.25 | Sodium methylparaben |
| 0.20 | Disodium EDTA |
| 0.15 | Fragrance |
| 0.15 | Sodium propylparaben |
| 0.10 | Sodium hydroxide |

Example 7

Grease-free Gel

| | |
|---|---|
| ad 100 | Water |
| 8.00 | Octyl methoxycinnamate |
| 7.00 | Titanium dioxide |
| 2.00 | Compound of Example 1 |
| 5.00 | Glycerol |
| 5.00 | PEG-25 PABA |
| 1.00 | 4-Methylbenzylidenecamphor |
| 0.40 | Acrylate $C_{10}$–$C_{30}$ alkyl acrylate crosspolymer |
| 0.30 | Imidazolidinylurea |
| 0.25 | Hydroxyethylcellulose |
| 0.25 | Sodium methylparaben |
| 0.20 | Disodium EDTA |
| 0.15 | Fragrance |
| 0.15 | Sodium propylparaben |
| 0.10 | Sodium hydroxide |

Example 8

Sun Cream

| | |
|---|---|
| ad 100 | Water |
| 8.00 | Octyl methoxycinnamate |
| 8.00 | Titanium dioxide |
| 6.00 | PEG-7 hydrogenated castor oil |
| 1.00 | Compound of Example 1 |
| 6.00 | Mineral oil |
| 5.00 | Zinc oxide |
| 5.00 | Isopropyl palmitate |
| 5.00 | Imidazolidinylurea |
| 3.00 | Jojoba oil |
| 2.00 | PEG-45/dodecyl glycol copolymer |
| 1.00 | 4-Methylbenzylidenecamphor |
| 0.60 | Magnesium stearate |
| 0.50 | Tocopheryl acetate |
| 0.25 | Methylparaben |

-continued

| | |
|---|---|
| 0.20 | Disodium EDTA |
| 0.15 | Propylparaben |

Example 9
Sun Cream

| | |
|---|---|
| ad 100 | Water |
| 8.00 | Octyl methoxycinnamate |
| 8.00 | Titanium dioxide |
| 6.00 | PEG-7 hydrogenated castor oil |
| 1.00 | Compound of the formula 1 |
| 6.00 | Mineral oil |
| 5.00 | Zinc oxide |
| 5.00 | Isopropyl palmitate |
| 5.00 | Imidazolidinylurea |
| 3.00 | Jojoba oil |
| 2.00 | PEG-45/dodecyl glycol copolymer |
| 1.00 | 4-Methylbenzylidenecamphor |
| 0.60 | Magnesium stearate |
| 0.50 | Tocopheryl acetate |
| 0.25 | Methylparaben |
| 0.20 | Disodium EDTA |
| 0.15 | Propylparaben |

Example 10
Water-resistant Sun Cream

| | |
|---|---|
| ad 100 | Water |
| 8.00 | Octyl methoxycinnamate |
| 5.00 | PEG-7 hydrogenated castor oil |
| 5.00 | Propylene glycol |
| 4.00 | Isopropyl palmitate |
| 4.00 | Caprylic/capric triglyceride |
| 1.50 | Compound of the formula 1 |
| 4.00 | Glycerol |
| 3.00 | Jojoba oil |
| 2.00 | 4-Methylbenzylidenecamphor |
| 2.00 | Titanium dioxide |
| 1.50 | PEG-45/dodecyl glycol copolymer |
| 1.50 | Dimethicone |
| 0.70 | Magnesium sulfate |
| 0.50 | Magnesium stearate |
| 0.15 | Fragrance |

Example 11
Water-resistant Sun Cream

| | |
|---|---|
| ad 100 | Water |
| 8.00 | Octyl methoxycinnamate |
| 5.00 | PEG-7 hydrogenated castor oil |
| 5.00 | Propylene glycol |
| 4.00 | Isopropyl palmitate |
| 4.00 | Caprylic/capric triglyceride |
| 1.00 | Compound of the formula 1 |
| 4.00 | Glycerol |
| 3.00 | Jojoba oil |
| 2.00 | 4-Methylbenzylidenecamphor |
| 2.00 | Titanium dioxide |
| 1.50 | PEG-45/dodecyl glycol copolymer |
| 1.50 | Dimethicone |
| 0.70 | Magnesium sulfate |

-continued

| | |
|---|---|
| 0.50 | Magnesium stearate |
| 0.15 | Fragrance |

Example 12
Sun Milk

| | |
|---|---|
| ad 100 | Water |
| 10.00 | Mineral oil |
| 6.00 | PEG-7 hydrogenated castor oil |
| 5.00 | Isopropyl palmitate |
| 3.50 | Octyl methoxycinnamate |
| 0.50 | Compound of Example 1 |
| 3.00 | Caprylic/capric triglyceride |
| 3.00 | Jojoba oil |
| 2.00 | PEG-45/dodecyl glycol copolymer |
| 0.70 | Magnesium sulfate |
| 0.60 | Magnesium stearate |
| 0.50 | Tocopheryl acetate |
| 0.30 | Glycerol |
| 0.25 | Methylparaben |
| 0.15 | Propylparaben |
| 0.05 | Tocopherol |

Example 13
Sun Milk

| | |
|---|---|
| ad 100 | Water |
| 10.00 | Mineral oil |
| 6.00 | PEG-7 hydrogenated castor oil |
| 5.00 | Isopropyl palmitate |
| 3.50 | Octyl methoxycinnamate |
| 0.50 | Compound of Example 1 |
| 3.00 | Caprylic/capric triglyceride |
| 3.00 | Jojoba oil |
| 2.00 | PEG-45/dodecyl glycol copolymer |
| 0.70 | Magnesium sulfate |
| 0.60 | Magnesium stearate |
| 0.50 | Tocopheryl acetate |
| 0.30 | Glycerol |
| 0.25 | Methylparaben |
| 0.15 | Propylparaben |
| 0.05 | Tocopherol |

Example 14
Water-resistant Sun Cream

| | |
|---|---|
| ad 100 | Water |
| 8.00 | Octyl methoxycinnamate |
| 5.00 | PEG-7 hydrogenated castor oil |
| 5.00 | Propylene glycol |
| 4.00 | Isopropyl palmitate |
| 4.00 | Caprylic/capric triglyceride |
| 2.00 | Compound of Example 1 |
| 4.00 | Glycerol |
| 3.00 | Jojoba oil |
| 2.00 | 4-Methylbenzylidenecamphor |
| 2.00 | Titanium dioxide |
| 1.50 | PEG-45/dodecyl glycol copolymer |
| 1.50 | Dimethicone |
| 0.70 | Magnesium sulfate |

-continued

| | |
|---|---|
| 0.50 | Magnesium stearate |
| 0.15 | Fragrance |

Example 15

Sun Milk

| | |
|---|---|
| ad 100 | Water |
| 10.00 | Mineral oil |
| 6.00 | PEG-7 hydrogenated castor oil |
| 5.00 | Isopropyl palmitate |
| 3.50 | Octyl methoxycinnamate |
| 2.00 | Compound of Example 1 |
| 3.00 | Caprylic/capric triglyceride |
| 3.00 | Jojoba oil |
| 2.00 | PEG-45/dodecyl glycol copolymer |
| 0.70 | Magnesium sulfate |
| 0.60 | Magnesium stearate |
| 0.50 | Tocopheryl acetate |
| 0.30 | Glycerol |
| 0.25 | Methylparaben |
| 0.15 | Propylparaben |
| 0.05 | Tocopherol |

We claim:

1. A process for protecting human skin or hair against solar rays which comprises application to said skin or hair a composition comprising as UV filter one or more enaminotriazines of the formula I

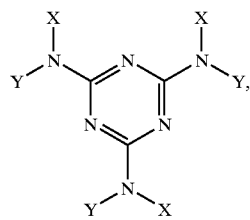

(I)

in which the radicals Y, independently of one another, are hydrogen, an optionally substituted aliphatic, cycloaliphatic, araliphatic or aromatic radical having in each case up to 18 carbon atoms, the radicals X are identical or different, where at least one of the radicals X is the ethenyl radical of the formula II

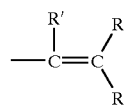

(II)

and X may also have the meanings of Y, and where in the formula II the radicals R are identical or different and are cyano, optionally esterified carboxyl, substituted carbonyl, optionally substituted aminocarbonyl, optionally esterified sulfo, substituted sulfonyl or optionally esterified phosphono, and where two adjacent radicals R may optionally form a ring and the radicals R' are identical or different and are hydrogen, an optionally substituted aliphatic, cycloaliphatic or aromatic radical having in each case up to 18 carbon atoms, optionally together with other compounds which absorb in the UV region.

2. The process as claimed in claim 1, wherein all radicals Y are hydrogen and all radicals X are the ethenyl radical of the formula II.

3. The process as claimed in claim 1 in which Y is hydrogen and one or more of the radicals X are an ethenyl radical of the formula IIa

(IIa)

in which the radicals $R^1$ and $R^2$ are identical or different and are —$COOR^4$, —$COR^4$, —$CON(R^4)_2$, —CN, —$SO_2R^4$, —$SO_2OR^4$ or —$PO(OR^4)_2$, where the radicals $R^4$, independently of one another, are hydrogen, an aliphatic, cycloaliphatic, araliphatic or aromatic radical, each of which may be optionally substituted, and where adjacent radicals $R^1$ and $R^2$ may optionally form a ring and $R^3$ is hydrogen or an aliphatic, cycloaliphatic, araliphatic or aromatic radical, each of which may be substituted.

4. The process as claimed in claim 3, wherein $R^3$ is hydrogen, $R^1$ and $R^2$ are identical or different and —$COOR^5$, —$COR^5$ or —CN, where $R^5$ is an aliphatic or optionally substituted aromatic radical having up to 18 carbon atoms.

5. A cosmetic or pharmaceutical preparation comprising light protection agents for protecting human skin or human hair against solar rays, which comprise, as essential UV filters, effective amounts of one or more enaminotriazines of the formula I

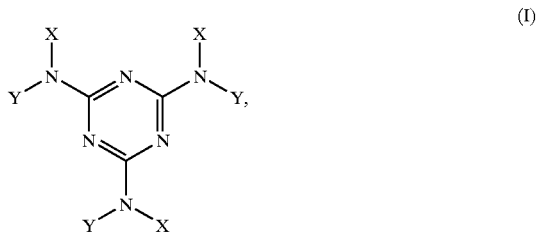

(I)

in which the radicals Y, independently of one another, are hydrogen, an optionally substituted aliphatic, cycloaliphatic, araliphatic or aromatic radical having in each case up to 18 carbon atoms, the radicals X are identical or different, where at least one of the radicals X is the ethenyl radical of the formula II

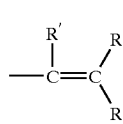

(II)

and X may also have the meanings of Y, and where in the formula II the radicals R are identical or different and are cyano, optionally esterified carboxyl, substituted carbonyl, optionally substituted aminocarbonyl, optionally esterified sulfo, substituted sulfonyl or optionally esterified phosphono, and where two adjacent radicals R may optionally form a ring, and the radicals R' are identical or different and are hydrogen, an optionally substituted aliphatic, cycloaliphatic or aromatic radical having in each case up to 18 carbon atoms, optionally, together other compounds which absorb in the UV region.

6. A cosmetic or pharmaceutical preparation comprising light protection agents as claimed in claim 5, which comprises enaminotriazines of the formula I in which all of the radicals Y are hydrogen and all of the radicals X are the ethenyl radical of the formula II.

7. A cosmetic or pharmaceutical preparation comprising light protection agents as claimed in claim 5, which comprises enaminotriazines of the formula I in which all of the radicals Y are hydrogen and one or more radicals X are the ethenyl radical of the formula IIa

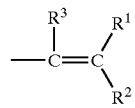
(IIa)

in which the radicals $R^1$ and $R^2$ are identical or different and are —$COOR^4$, —$COR^4$, —$CON(R^4)_2$, —CN, —$SO_2R^4$, —$SO_2OR^4$ or —$PO(OR^4)_2$, where the radicals $R^4$, independently of one another, are hydrogen, an aliphatic, cycloaliphatic, araliphatic or aromatic radical, each of which may be optionally substituted, and where adjacent radicals $R^1$ and $R^2$ may optionally form a ring and $R^3$ is hydrogen or an aliphatic, cycloaliphatic, araliphatic or aromatic radical, each of which may be substituted.

8. A cosmetic or pharmaceutical preparation comprising light protection agents as claimed in claim 7, wherein $R^3$ is hydrogen, $R^1$ and $R^2$ are identical or different and —$COOR^5$, —$COR^5$ or —CN, where $R^5$ is an aliphatic or optionally substituted aromatic radical having up to 18 carbon atoms.

* * * * *